United States Patent [19]

McGredy, IV

[11] Plant 4,669

[45] Mar. 17, 1981

[54] ROSE PLANT

[75] Inventor: Samuel McGredy, IV, Auckland, New Zealand

[73] Assignee: Armstrong Nurseries, Inc., Ontario, Calif.

[21] Appl. No.: 112,750

[22] Filed: Jan. 17, 1980

[51] Int. Cl.[3] ..... A01H 5/00

[52] U.S. Cl. ..... Plt./2

[58] Field of Search ..... Plt./14

*Primary Examiner*—James R. Feyrer

*Attorney, Agent, or Firm*—William H. Elliott, Jr.; Andrew R. Klein

[57] ABSTRACT

A hybrid rose plant of the climber class, having a very vigorous growth habit with long arching canes and dense foliage. Flowers are of moderate size, from 2 to 3 inches, and are borne mostly in clusters of 5 or more to a stem, readily creating a mass display. The blooms have a strong bi-color effect, dominated by bright orange intermixed with white. The plant flowers almost continuously during the growing season.

1 Drawing Figure

This invention relates to a new and distinct variety of rose plant of the climber class. The plant is a half-hardy tall outdoor seedling having as its seed parent "Liverpool Echo" and as its pollen parent, an unnamed and undisseminated seedling which iself descended from "Evelyn Fison" x ("Orange Sweetheart" x "Fruhlingsmorgen"). "Evelyn Fison" is represented by U.S. Plant Pat. No. 2,424 and "Orange Sweetheart" by U.S. Plant Pat. No. 1,155. The new cultivar was first propagated by Samuel McGredy, IV, in Portadown, Ireland. The plant described herein was grown in Ontario, Calif., from budwood of that crossing. It holds its distinguishing characteristics through succeeding propagations by budding.

The new cultivar bears its flowers sometimes singly but usually five or more to a stem, in flat clusters, on strong, medium to long stems. It blooms abundantly outdoors, and almost continuously during the growing season. Its blooms have a slight tea fragrance.

Among the ways in which the new cultivar may be distinguished from its seed parent, "Liverpool Echo" are the following characteristics:

"Liverpool Echo" bears flowers of salmon-orange coloration, whereas the new rose bears bicolored orange and white flowers essentially as described.

"Liverpool Echo" has significantly larger flowers, being of 4 inch diameter as compared to the new rose which bears 2 or 3 inch diameter flowers. Among the ways in which this new cultivar may be distinguished from the named cultivars in the ancestry of its pollen parent, which itself is an unnamed, undisseminated seedling, are the following:

Whereas the flowers of the new rose have 18 to 25 petals with the unique coloration described herein, "Evelyn Fison" has 10 to 12 petals of relatively uniform scarlet coloration. Further, the flower cluster of the new cultivar is significantly smaller than the broad flower clusters of "Evelyn Fison". Further, "Evelyn Fison" has a significantly lower and more compact plant habit than does the new rose.

"Orange Sweetheart" bears 3 to 3½ inch diameter flowers of a uniform orange-pink coloration, whereas the new rose bears significantly smaller flowers of 2 to 3 inch diameter and of the unique orange and white coloration described herein. Furthermore, "Orange Sweetheart" has a significantly lower and more compact habit of growth than does the new rose.

Whereas the new cultivar bears double flowers of bicolor orange and white coloration "Fruhlingsmorgen" bears single flowers of cherry-pink coloration with a soft yellow petal base. Furthermore, "Fruhlingsmorgen", a hybrid of "*Rosa spinosissima*", blooms only once during the growing season, whereas the new rose blooms nearly continuously throughout the growing season.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is short to average length and of average to heavy caliper. It is erect and stiff, almost smooth, with very few hairs. Its color is between Moderate Yellow Green, 2.5GY5/5 and Strong Yellow Green, 2.5GY6/8.

Before the calyx breaks, the bud is of small to medium size, moderately short, globular and with foliaceous appendages, and few stipitate glands on the surface of the bud, usually with slender foliaceous parts extending beyond the tip of the bud up to ¼ or its length.

As the calyx breaks, the color is near Strong Red, 5R4/12.

The sepals on their inner surface have a wooly tomentum the margins being lined with stipitate glands and hairs.

As the first petal opens, the size is average and the form is of medium length and ovoid. The color on the outside is predominantly near Moderate Pink, 2.5R8/5, with some markings of between Moderate Pink, 5R8/6, and Strong Red, 2.5R5/12.

Inside, the base of the bud is near Brilliant Greenish Yellow, 7.5Y9/8, the remainder being between Strong Reddish orange, 7.5R5/13, and Dark Reddish Orange, 7.5R4/11. The bud opens well. It is not retarded or prevented from opening by cold, hot, wet or dry weather.

BLOOM

When fully open, the bloom is of average size, about 2 inches to 3 inches across. The petalage is double, ranging from 18 to 25 petals plus 0 to 3 petaloids, arranged irregularly. The form of the bloom is cupped at first becoming flat to cupped with the petals remaining at first somewhat loosely cupped becoming later, at maturity, more loosely cupped.

The texture of the petals is thick with the inside satiny and the outside slightly shiny. The shape of the petals on the outside is round to broadly obovate with apex flat. The intermediate petals are broadly ovate with apex flat. The inside petals are broadly obovate with apex rounded.

The colors may be modified by being shaded and/or washed or tinted with other colors.

The following description applies to a newly opened flower in the month of July. The rose had been grown outdoors in Ontario, Calif.

The coloration of the outside petal as to its outer surface is between White and Moderate Pink, 2.5R9/3. The outer surfaces of the intermediate petal and of the inside petal were of the same coloration.

The inner surface of the outside petal was Brilliant Greenish Yellow, 7.5Y9/8 at the base, with the remainder between Strong Reddish Orange, 7.5R6/12, and Dark Reddish Orange, 7.5R4/11. The inner surfaces of the intermediate and inner petals were of the same coloration.

The following description was made from a rose that had been open for three days outdoors in the month of July in Ontario, Calif.

The outer surface of the outside petal was near Brilliant Greenish yellow, 7.5Y9/8, at the base, the remainder being between White and Deep Pink, 2.5R6/11. The outer surface of the inside petal was of the same coloration.

The inner surface of the outside petal was near Brilliant Greenish Yellow, 7.5Y9/8, at the base, the remainder being between Strong Reddish Orange, 7.5R6/12, and Vivid Red, 5R5/13. The inner surface of the inside petal was of the same coloration.

The general color effect of the newly opened flower was near Strong Reddish Orange, 7.5R5/13, with a distinct center between White and Brilliant Greenish Yellow, 7.5Y9/8. After being open for three days, the coloration was between Strong Reddish Orange, 7.5R5/13, and Vivid Red 5R1/13, with a distinct center of near Brilliant Greenish Yellow, 7.5Y9/8. The petals persist, fading to near Strong Yellowish Pink, 7.5R7/9. The bloom is not particularly affected by cold, hot, wet or dry weather.

Flowers on the bush in the garden persist from 3 to 5 days in the month of July. Cut roses grown outdoors and kept at living-room temperatures last from 3 to 5 days in August.

REPRODUCTIVE ORGANS

Stamens are of average number to many, arranged regularly about the pistils.

The filaments are of short to medium length and the color is between Brilliant Greenish Yellow, 7.5Y9/8, and Brilliant Yellow, 5Y9/9. Most of them are with anthers.

The anthers are small to medium in size, all opening at once approximately. The color just prior to dehiscence at the central portion is near Strong Greenish Yellow, 10Y8/11. At the outer edge, it is near Brilliant Yellow, 5Y9/9.

The pollen is sparse to moderate and near Brilliant Greenish Yellow, 7.5Y9/8, in color.

The pistils are of average number, there being approximately 70.

The styles are moderately uneven, short to average length and average caliper, somewhat loosely bunched. The color is near Brilliant Greenish Yellow, 7.5Y9/8.

The stigma is near Brilliant Greenish Yellow, 10Y9/9.

The ovaries are mostly enclosed in the calyx.

The immature hips are short, ovoid and between Brilliant Yellow Green, 2.5GY8/9, and Strong Yellow Green, 2.5GY7/10. They have moderately smooth walls which are thick and fleshy.

The sepals are permanent, of medium length and spear-shaped. The inside color is near Brilliant Yellow Green, 2.5GY9/8, with a heavy gray overcast. The color outside is between Brilliant Yellow Green, 2.5GY8/9, and Strong Yellow Green, 2.5GY7/10.

The seeds are of average number to many, usually small and there are from 10 to 18 of them.

FOLIAGE

The compound leaves consist of usually 3 to 7 leaflets. They are abundant in number and medium size to large. They are heavy to somewhat leathery in texture and semi-glossy.

The leaflets are ovate to obovate in form with apex mucronate, base acute, the margin doubly serrate.

The color of the mature foliage on its upper surface is between Dark Yellowish Green, 10GY4/5 and Moderate Olive Green, 2.5GY4/3, on its lower surfaces the mature foliage is near Moderate Olive Green, 5GY4/3, washed heavily with grey. The color of the young foliage on its upper surface is near Dark Red, 5R3/7 washed with near Moderate Olive Brown, 2.5Y4/4. On its under surface, the color is near Dark Red, 5R3/7.

The rachis is of average size and on its upper side is grooved with some stipitate glands on the edges. On its under side the rachis is extremely smooth.

The stipules are of medium length, moderately narrow with medium-length points, turning out at an angle of less than 45°.

As to disease resistence, this variety displays more than average resistance to mildew as compared to similar plants grown in the Ontario area under comparable conditions.

GROWTH

The plant is of bushy, upright habit, tending to climbing. The growth is very vigorous. The canes are heavy in caliper.

The main stems are near Strong yellow Green, 2.5GY6. The large prickles are few in number, with a medium to long length and are straight with medium-length narrow base. Their color is near Moderate Yellow Brown, 10YR4/4, washed heavily with gray. There are no small prickles and no hairs.

The branches have a color between Brilliant Yellow Green, 5GY8/8, and Strong Yellow Green, 5GY6/8. They carry large prickles, few to several in number, of medium length to long, straight, and with a medium-length, moderately narrow base. The color of the base and point are near Brilliant Yellow Green, 2.5GY9/8, the remainder being washed with near Deep Yellowish Pink, 5R6/11.

There are no small prickles and no hairs.

The new shoots are near Moderate Yellow Green, 5GY5/6, in color. They carry few to several large prickles of medium-length to long dimension, straight with medium-length narrow base. The color of the point is near Brilliant Yellow Green, 2.5GY9/8. The remainder is near Moderate Red, 2.5R4/10. There are only a few small prickles, of the same color as the large prickles. There are no hairs.

I claim:

1. A new and distinct variety of rose plant of the climber class, substantially as herein shown and described, said plant being especially characterized by the vigor of its growth habit, the abundance of its foliage, and most particularly by the bi-color effect of its flowers, which are of double petalage, a coloration dominated by bright orange, intermixed with white, said flowers being borne mostly in clusters of five or more to a stem.

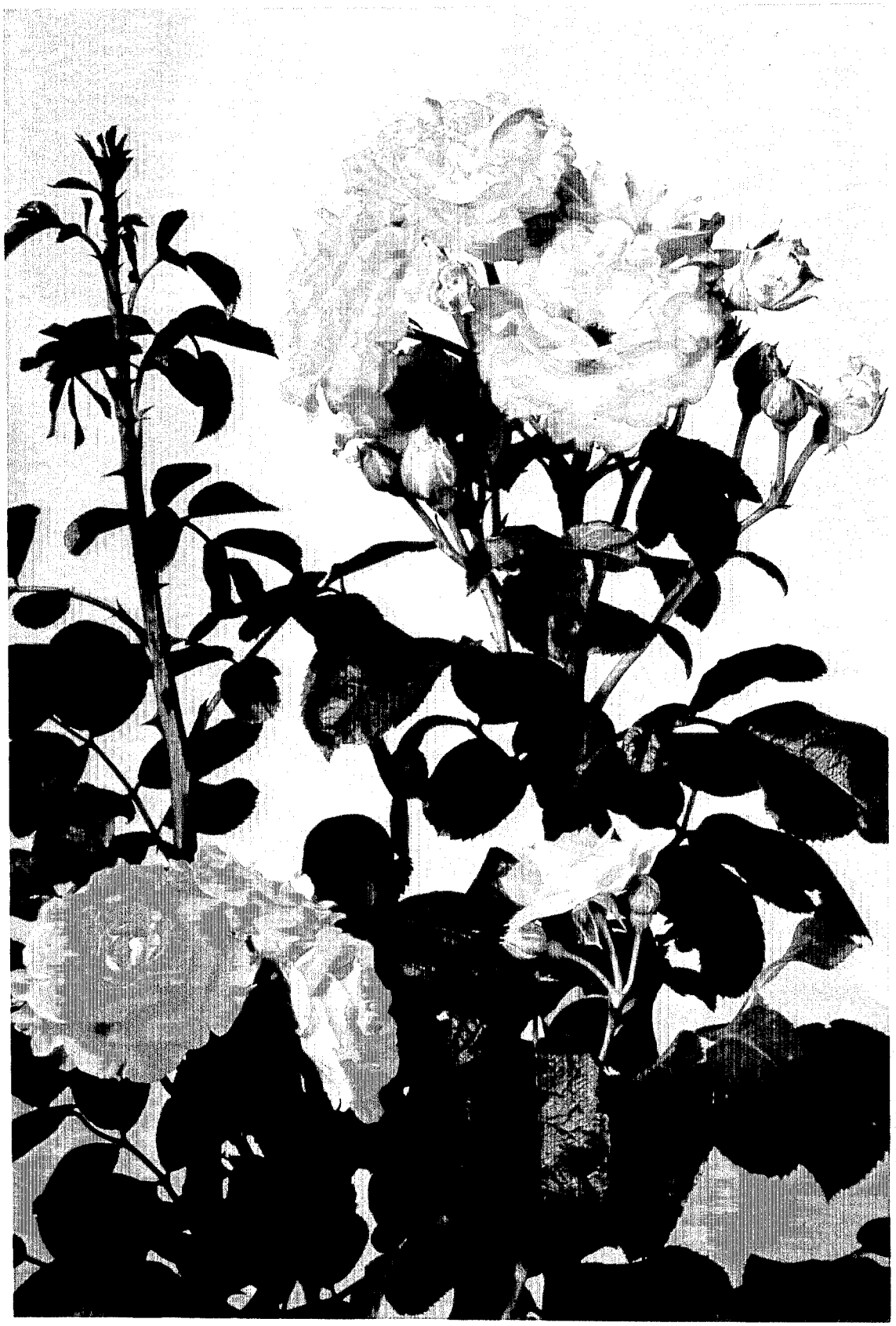

* * * * *